(12) United States Patent
Albertson

(10) Patent No.: US 8,113,708 B2
(45) Date of Patent: Feb. 14, 2012

(54) CLOUD POINT MONITORING SYSTEMS FOR DETERMINING A CLOUD POINT TEMPERATURE OF DIESEL FUEL

(75) Inventor: William C. Albertson, Clinton Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 857 days.

(21) Appl. No.: 12/174,244

(22) Filed: Jul. 16, 2008

(65) Prior Publication Data
US 2010/0014554 A1   Jan. 21, 2010

(51) Int. Cl.
*G01N 25/00* (2006.01)
(52) U.S. Cl. ............................................ 374/16; 374/20
(58) Field of Classification Search ............... 374/16–17, 374/20, 28, 43–45, 54; 184/6.4; 73/54.07, 73/54.01, 54.02, 61.45; 702/50
See application file for complete search history.

(56) References Cited

U.S. PATENT DOCUMENTS

| | | | | |
|---|---|---|---|---|
| 3,983,501 A | | 9/1976 | Lindstrum | |
| 4,484,821 A | * | 11/1984 | Willcock | 374/24 |
| 5,661,233 A | * | 8/1997 | Spates et al. | 73/61.45 |
| 5,827,952 A | * | 10/1998 | Mansure et al. | 73/61.45 |
| 5,887,572 A | * | 3/1999 | Channing | 123/514 |
| 6,827,484 B2 | * | 12/2004 | Tsang et al. | 374/20 |
| 6,966,692 B2 | * | 11/2005 | Tsang et al. | 374/20 |
| 2008/0093172 A1 | * | 4/2008 | Albertson et al. | 184/6.4 |
| 2008/0223114 A1 | * | 9/2008 | Albertson et al. | 73/54.07 |
| 2010/0012410 A1 | * | 1/2010 | Pryor et al. | 180/69.4 |
| 2010/0014553 A1 | * | 1/2010 | Pryor et al. | 374/16 |
| 2010/0033372 A1 | * | 2/2010 | Pryor et al. | 342/357.09 |

OTHER PUBLICATIONS

W. Mahmood Mat Yunus and Maulana Ahmad, "A Simple Ultrasonic Experiment Using a Phase Shift Detection Technique", Universiti Pertanian Malaysia, Selangor, Malaysia, New Approaches, pp. 202-206; Dec. 6, 1995.

\* cited by examiner

*Primary Examiner* — Lisa Caputo
*Assistant Examiner* — Tania Courson
(74) *Attorney, Agent, or Firm* — Cantor Colburn LLP

(57) ABSTRACT

Cloud point monitoring systems for determining a cloud point temperature value for diesel fuel are provided. In one exemplary embodiment, a cloud point monitoring system receives diesel fuel in the tubular conduit and propagates a sound wave through the diesel fuel. The cloud point monitoring system further determines a cloud point temperature value indicative of a cloud point of the diesel fuel based on a phase shift of the sound wave propagating through the diesel fuel.

21 Claims, 4 Drawing Sheets

US 8,113,708 B2

CLOUD POINT MONITORING SYSTEMS FOR DETERMINING A CLOUD POINT TEMPERATURE OF DIESEL FUEL

FIELD OF THE INVENTION

Exemplary embodiments of the present invention relate generally to diesel fuel systems, and more particularly to diesel fuel cloud point monitoring systems.

BACKGROUND

At relatively cold ambient temperatures diesel fuel can partially solidify (gel) due to the formation of waxy crystals. Gelling of the fuel can affect engine performance, including causing the engine to cease operation. Formation of the waxy crystals causes the fuel to become cloudy. The cloud point temperature of the fuel is the temperature at which the wax crystals begin to form. The cloud point temperature of diesel fuel can vary widely even within fuel of the same grade (i.e., No. 2 diesel), and also varies widely when biodiesel fuels are mixed with diesel fuel. Diesel fuels are generally blended so as to have a cloud point temperature which is appropriate for the location in which the fuel is sold. Therefore, it may be desirable to detect and monitor the cloud point temperature of the diesel fuel, since vehicles may take on fuel in a relatively warmer region where gelling is not a concern and due to their long travel range carry the fuel blended for the warmer region to relatively colder regions where gelling is possible. A problem associated with some existing cloud point monitoring devices is that wax crystals can form in such a way that they may not be detected in the diesel fuel, resulting in an inaccurate determination of the cloud point temperature, thereby limiting the ability to take appropriate measures to prevent gelling of the diesel fuel.

Accordingly, it is desirable to develop cloud point monitoring systems having improved accuracy with regard to detection and monitoring of the cloud point temperature.

SUMMARY OF THE INVENTION

A cloud point monitoring system in accordance with an exemplary embodiment of the present invention is provided. The cloud point monitoring system includes a conduit, having a first aperture and a second aperture, the apertures configured to admit diesel fuel from a fuel conduit into and through the conduit. The cloud point monitoring system further includes an acoustic source disposed in the conduit. The acoustic source is configured to emit an oscillatory sound wave in response to a first oscillatory signal from a controller. The cloud point monitoring system further includes an acoustic sensor disposed in the conduit and spaced from the acoustic source. The acoustic sensor is configured to receive the oscillatory sound wave emitted from the acoustic source and to generate a responsive oscillatory signal to the oscillatory sound wave. The cloud point monitoring system further includes a temperature sensor disposed in the conduit and configured to generate a temperature signal indicative of the temperature of the diesel fuel in the conduit. The cloud point monitoring system further includes a controller configured to generate and send the first oscillatory signal to the acoustic source. The controller is further configured to receive the responsive oscillatory signal from the acoustic sensor and to determine a phase shift of the sound wave based on the first oscillatory signal and the responsive oscillatory signal. The controller is further configured to receive the temperature signal from the temperature sensor and to thereby determine a cloud point temperature value associated with the diesel fuel in the conduit based on the phase shift of the oscillatory wave and the temperature signal.

A motor vehicle in accordance with another exemplary embodiment of the present invention is provided. The motor vehicle includes a diesel engine configured to receive diesel fuel from a fuel tank through a fuel conduit. The motor vehicle further includes a cloud point monitoring system receiving a portion of the diesel fuel from the fuel conduit. The cloud point monitoring system includes a conduit, having a first aperture and a second aperture, the apertures configured to admit diesel fuel from a fuel conduit into and through the conduit. The cloud point monitoring system further includes an acoustic source disposed in the conduit. The acoustic source is configured to emit an oscillatory sound wave in response to a first oscillatory signal from a controller. The cloud point monitoring system further includes an acoustic sensor disposed in the conduit and spaced from the acoustic source. The acoustic sensor is configured to receive the oscillatory sound wave emitted from the acoustic source and to generate a responsive oscillatory signal to the oscillatory sound wave. The cloud point monitoring system further includes a temperature sensor disposed in the conduit and configured to generate a temperature signal indicative of the temperature of the diesel fuel in the conduit. The cloud point monitoring system further includes a controller configured to generate and send the first oscillatory signal to the acoustic source. The controller is further configured to receive the responsive oscillatory signal from the acoustic sensor and to determine a phase shift of the sound wave based on the first oscillatory signal and the responsive oscillatory signal. The controller is further configured to receive the temperature signal from the temperature sensor and to thereby determine a cloud point temperature value associated with the diesel fuel in the conduit based on the phase shift of the oscillatory wave and the temperature signal.

BRIEF DESCRIPTION OF THE DRAWINGS

Other features, advantages and details appear, by way of example only, in the following description of embodiments, the description referring to the drawings in which.

DESCRIPTION OF THE EMBODIMENTS

Figure 1:
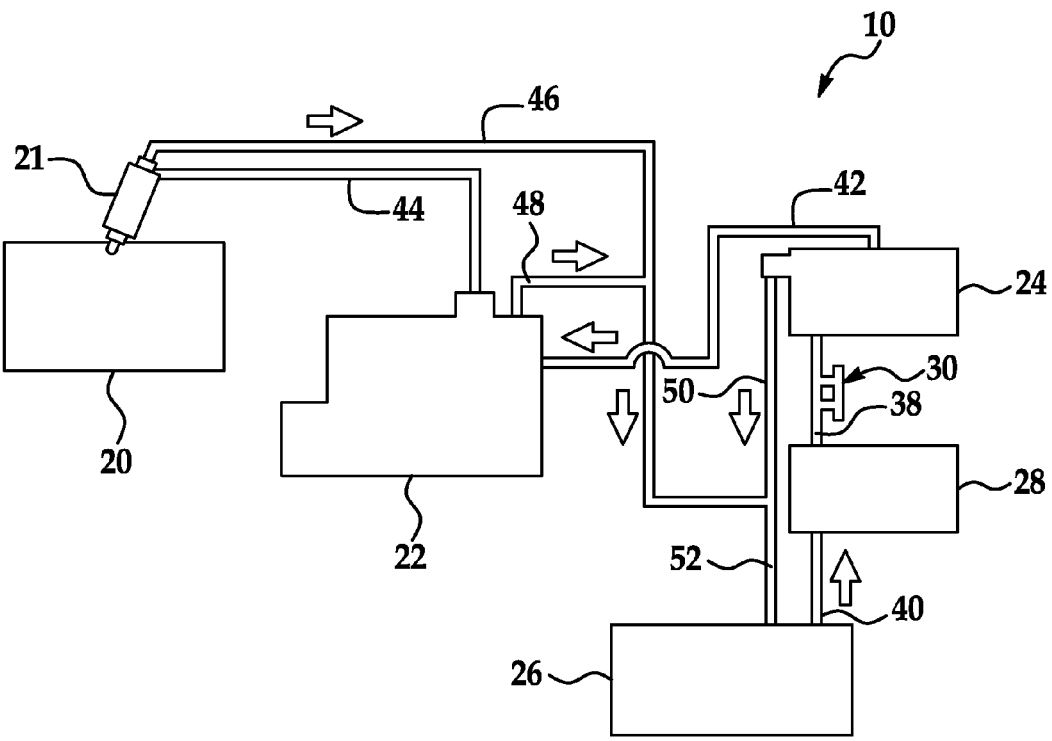
FIG. 1 is a schematic of vehicle having a cloud point monitoring system in accordance with an exemplary embodiment.

Referring to FIG. 1, a vehicle 10 having a cloud point monitoring system 30 in accordance with an exemplary embodiment is provided. The vehicle 10 further includes an engine 20, a fuel injector 21, a fuel pump 22, a fuel filter 24, a fuel tank 26, a feed pump 28, tubular conduits 40, 42, 44, 46, 48, 50, 52 which fluidly interconnect various of the aforementioned components for communication of diesel fuel between them and a diesel fuel conduit 38. Conduits 38, 42, 44, 46, 48, 50 and 52 are described herein as tubular conduits, but any suitable conduit may be employed, including conduits of other cross-sectional shapes. Associated with diesel fuel conduit 38 is a cloud point monitoring system 30 which is provided to determine and monitor a cloud point temperature for diesel fuel utilized by the vehicle 10. While cloud point monitoring system 30 is associated with diesel fuel conduit 38 in the exemplary embodiments shown, association with other tubular conduits of a fuel system is also believed to be possible and within the scope of the present invention. Further, while illustrated in the various exemplary embodiments described herein in conjunction with engine 20 for vehicle 10, cloud point monitoring system 30 may be employed in fuel systems for all manner of diesel engines.

The fuel injector 21, fuel pump 22, fuel filter 24, fuel tank 26, fuel pump 28, tubular conduits 40, 42, 44, 46, 48, 50 and 52, diesel fuel conduit 38 and monitoring system 30 are elements of a fuel system for delivering diesel fuel to engine 20. The feed pump 28 fluidly communicates with the tubular conduit 40 and the diesel fuel conduit 38. The feed pump 28 is configured to pump diesel fuel from the fuel tank 26 through the tubular conduit 40 and the diesel fuel conduit 38 to the fuel filter 24.

The fuel filter 24 fluidly communicates with the diesel fuel conduit 38 and the tubular conduits 42, 50. The fuel filter 24 is configured to filter the diesel fuel flowing therethrough and to allow a portion of the diesel fuel to flow through the tubular conduit 42 to the fuel pump 22. The fuel filter 24 is further configured to return a portion of the received diesel fuel through the tubular conduits 50, 52, to the fuel tank 26.

The fuel pump 22 fluidly communicates with the tubular conduits 42, 44 and 48. The fuel pump 22 is configured to pump diesel fuel through the tubular conduit 44 to the fuel injector 21. The pressure of the diesel fuel within the tubular conduit 44 is at a relatively high pressure level. The diesel pump 22 is further configured to return some residual diesel fuel through the tubular conduits 48, 52 to the fuel tank 26.

The fuel injector 21 is operably coupled to the engine 20 and fluidly communicates with the tubular conduits 44, 46. The fuel injector 21 is configured to receive diesel fuel from the fuel pump 22 via the tubular conduit 44 at a relatively high pressure level. The fuel injector 21 is further configured to inject a first portion of the received diesel fuel into the engine 20. A second portion of diesel fuel received by the fuel injector 21 is routed through the tubular conduits 46, 52 back to the fuel tank 26.

Figure 3:
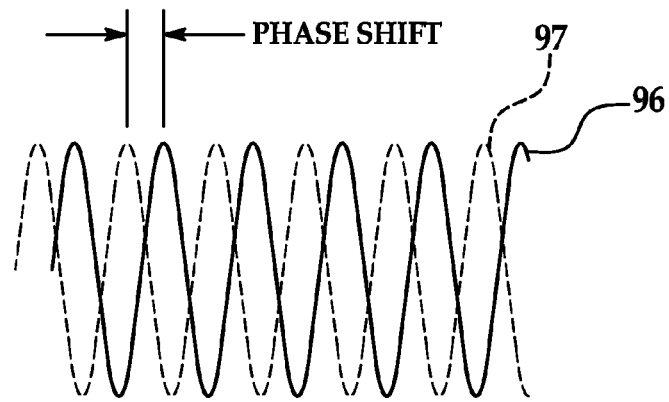
FIG. 3 is a signal schematic of a sound wave phase shift in the cloud point monitoring system of FIG. 2.
Figure 4:
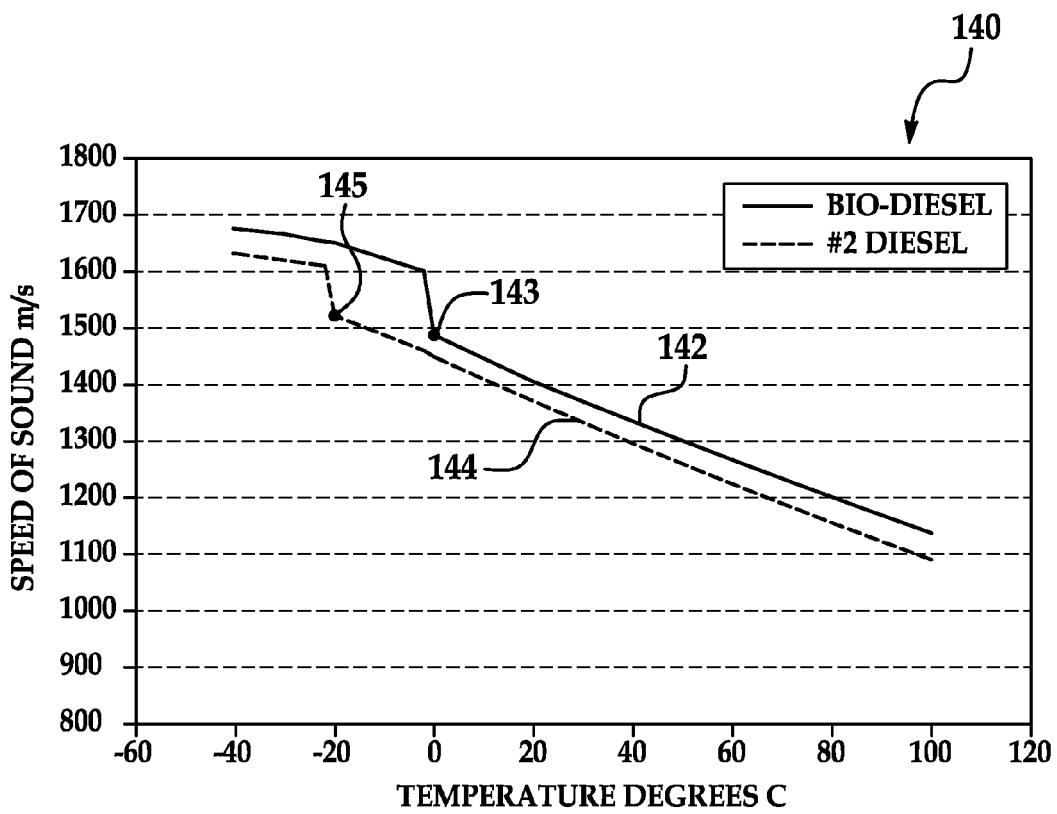
FIG. 4 is a graph of curves illustrating a speed of sound in first and second diesel fuel types over varying temperatures.

Referring to FIG. 3, before providing a detailed explanation of the cloud point monitoring system 30, a general overview of the physical characteristics of sound waves in diesel fuel will now be explained. As an oscillatory acoustic wave signal, represented by curve 96, propagates through a medium such as diesel fuel from an acoustic wave source, typically a transducer such as a speaker, to an acoustic wave receiver, typically a transducer such as a microphone, which is spaced from the source and receives the oscillatory acoustic wave signal, represented by curve 97, a phase shift results. The phase shift is associated with the speed of sound in the medium, the spacing of the source and the receiver and the frequency of the oscillatory acoustic wave signal. Further, as shown in FIG. 4, in a medium such as liquid diesel fuel or biodiesel fuel, the density changes as a function of temperature, generally increasing with decreasing temperature, resulting in an increase in the speed of sound in the fuel and a decrease in the phase shift between the source signal and received signal. In particular, when diesel fuel is at or below a cloud point temperature, a phase change occurs such that wax crystals form in the diesel fuel and it changes from a liquid to a waxy semi-solid state. This change causes the bulk modulus of the fuel to increase dramatically, thus appreciably increasing the speed of sound through the fuel and appreciably decreasing the phase shift. Referring to FIG. 4, this marked change in the speed of sound is reflected in exemplary plots of the speed of sound as a function of temperature for a biodiesel formulation 142 and a No. 2 diesel formulation 144, by inflection points 143 and 145 respectively. For these formulations, for a given arrangement of the source and detector spacing and acoustic wave input, the phase shifts which occur at temperatures above or to the right of the respective inflection points are greater than the phase shifts which occur at temperatures below or to the left of the inflection point. Thus, for a particular formulation, when the magnitude of the phase shift of the transmitted oscillatory sound wave is less than a predetermined phase shift, such as that associated with the inflection point, the diesel fuel is at or below a cloud point temperature. The foregoing phase shift characteristic associated with oscillatory sound waves traveling through diesel fuel is utilized by the cloud point monitoring system 30 to determine the cloud point temperature of the diesel fuel.

Figure 2:
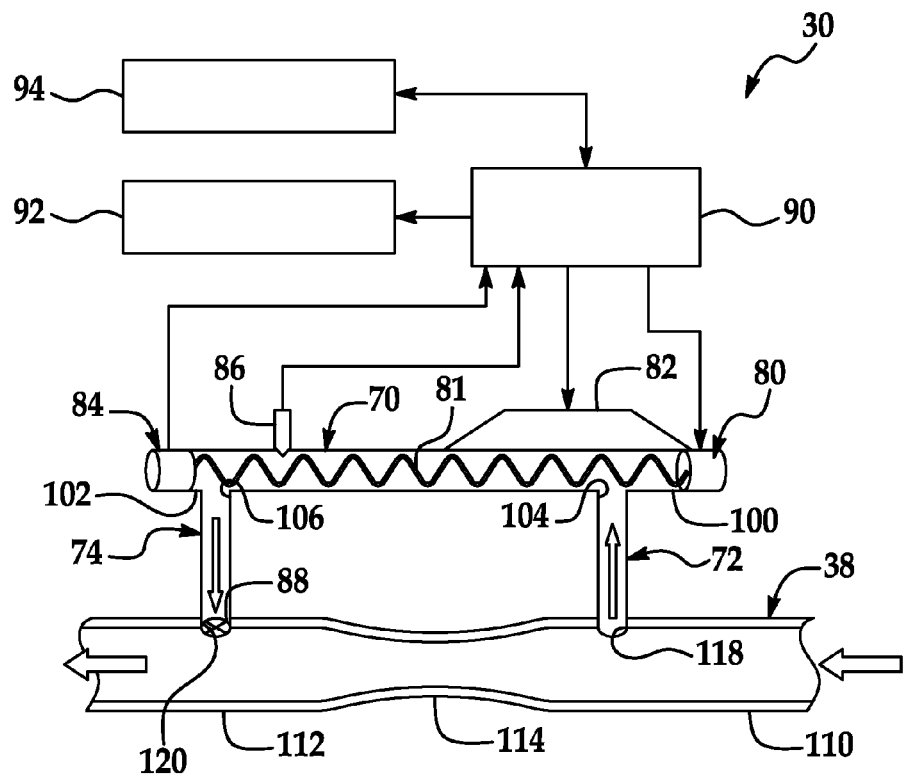
FIG. 2 is a schematic of the cloud point monitoring system utilized in the vehicle of FIG. 1.

Referring to FIG. 2, the cloud point monitoring system 30 which determines a cloud point temperature of diesel fuel will now be explained in greater detail. The cloud point monitoring system 30 includes tubular conduits 70, 72, 74, an acoustic wave source or output device such as electrical speaker 80, a thermal device 82, an acoustic sensor such as microphone 84, a temperature sensor 86, a filter 88, a controller 90, a display device 92, and a memory device 94. The cloud point monitoring system 30 is fluidly coupled to the diesel fuel conduit 38 and receives a portion of the diesel fuel flowing through the diesel fuel conduit 38, to determine the cloud point temperature of the diesel fuel.

The tubular conduit 72 is disposed between the diesel fuel conduit 38 and the tubular conduit 70. The tubular conduit 72 is configured to receive a portion of the diesel fuel flowing through diesel fuel conduit 38 via the aperture 118 in the end portion 110 of the diesel fuel conduit 38 and to route this portion of the diesel fuel through the aperture 104 and into the tubular conduit 70. The aperture 104 is disposed proximate to the first end 100 of the tubular conduit 70.

The tubular conduit 74 is disposed between the diesel fuel conduit 38 and the tubular conduit 70. The tubular conduit 74 is configured to receive the diesel fuel in tubular conduit 70 via the aperture 106 in the second end 102 of the tubular conduit 70 and to route the diesel fuel through the aperture 120 and back into the diesel fuel conduit 38. The aperture 106 is disposed proximate the second end 102 of the tubular conduit 70. As a result, diesel fuel flows through conduit 70 from the first end 100 toward the second end 102.

In a preferred configuration, the acoustic wave source in the form of electrical speaker 80 is disposed at the end 100 of the tubular conduit 70 and is configured so as to be operative for communication of acoustic waves into the diesel fuel in the tubular conduit 70. The electrical speaker 80 is configured to emit an oscillatory sound wave 81 having a predetermined frequency in the tubular conduit 70 that propagates towards the second end 102 of the tubular conduit 70, in response to receiving an oscillatory control signal from the controller 90.

The thermal device 82 is disposed adjacent to the tubular conduit 70 and is configured to cool the tubular conduit 70 and the diesel fuel therein, in response to receiving a control signal from the controller 90. In one exemplary embodiment, the thermal device 82 is a Peltier cell, however, other suitable means for cooling may also be employed within the scope of the present invention.

The acoustic sensor in the form of microphone 84 is spaced from acoustic wave source 80 and may be disposed proximate to the second end 102 of the tubular conduit 70. The microphone 84 is configured to receive oscillatory sound wave 81 and generate a responsive oscillatory signal which is indicative of the frequency of the wave in response thereto. The microphone 84 transmits the oscillatory signal to the controller 90.

The temperature sensor 86 is disposed on the tubular conduit 70 and fluidly communicates with the diesel fuel therein. The temperature sensor 86 is configured to generate a signal indicative of a temperature of the diesel fuel in the tubular conduit 70, which is received by the controller 90. In one exemplary embodiment, temperature sensor 88 comprises a thermocouple.

The filter 88 is disposed across the aperture 120 of the diesel fuel conduit 38. The filter 88 is configured to trap wax crystals that may be formed in the diesel fuel flowing through the tubular conduit 70 in conjunction with the operation of thermal device 82.

The controller 90 is electrically coupled to and operative for signal communication with the speaker 80, the thermal device 82, the microphone 84, the temperature sensor 86, the display device 92 and the memory device 94. The controller 90 is provided to determine a cloud point temperature of the diesel fuel based on signals received from the temperature sensor 86 and the microphone 84, as will be explained in greater detail below. In one exemplary embodiment, the controller 90 comprises a microprocessor. The memory device 94 is provided to store data and values generated by controller 90 therein. The display device 92 is provided to display data and values generated by the controller 90.

The diesel fuel conduit 38 includes the end portion 110, the end portion 112, and a restricted portion 114. The restricted portion 114 is disposed between the end portions 110, 112. The restricted portion 114 causes a pressure drop in the diesel conduit 38 which induces diesel fuel to flow from end portion 110 to end portion 112 through the tubular conduits 72, 70 and 74. The cloud point monitoring system 30 of the present invention is particularly advantageous in that it enables measurement of the cloud point temperature of the fuel in a conduit which is similar to conduits used throughout the fuel system and under similar fluid flow conditions, thereby reducing or eliminating any effect of the fluid flow conditions on the measurement of the cloud point temperature. However, cloud point monitoring system 30 is in a separate branch of the fuel system and associated fuel conduits such that the process of monitoring and the formation of waxy crystals will have minimal impact on the performance of the fuel system. For example, any reduction in flow associated with monitoring and the formation of waxy crystals in the fuel will only affect flow through the cloud point monitoring system 30 and not the overall fuel system.

Figure 5:
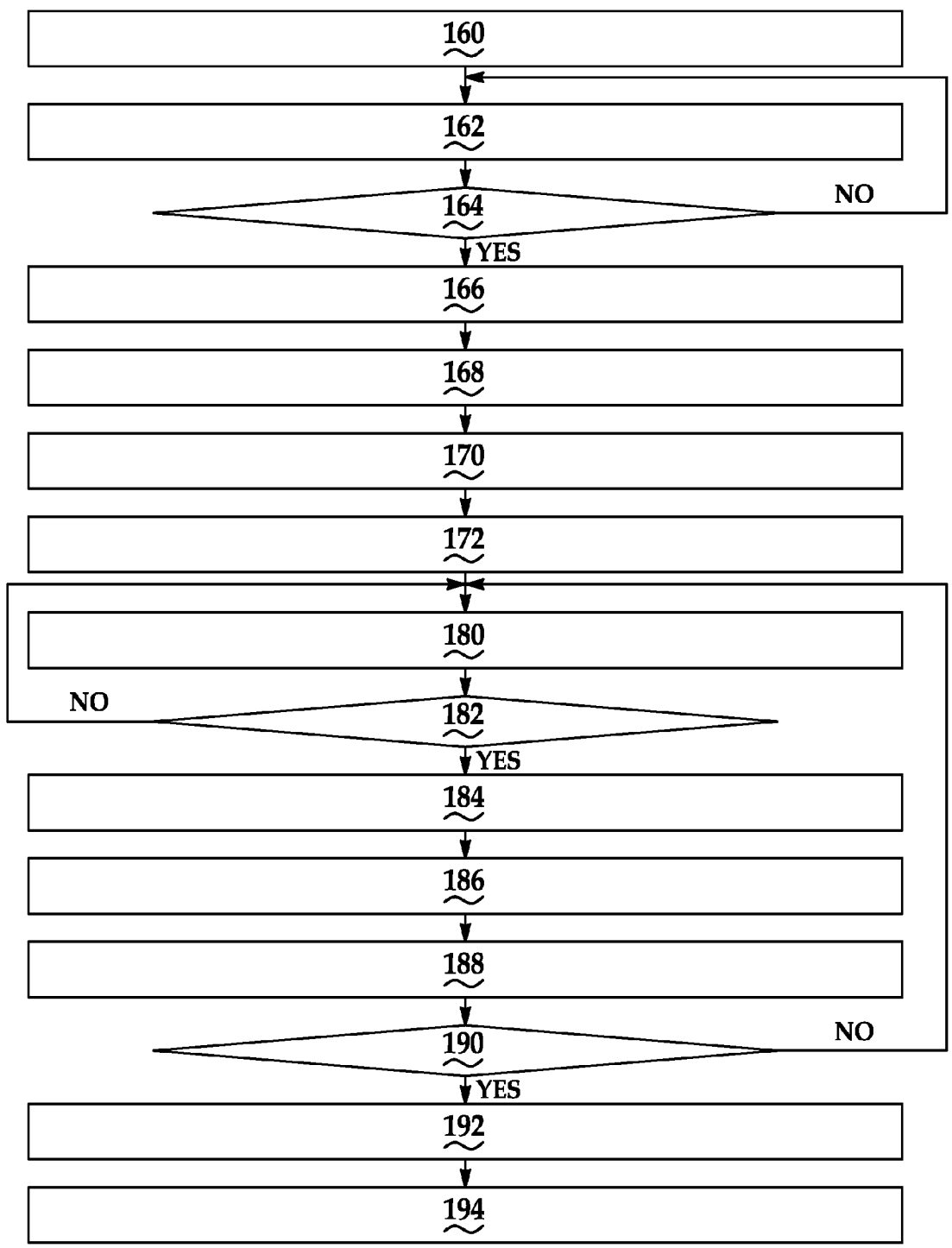
FIG. 5 is a flowchart of a method for determining a cloud point temperature value for diesel fuel in accordance with another exemplary embodiment.

Referring to FIGS. 2 and 5, a flowchart of a method for determining a cloud point temperature value for diesel fuel in accordance with another exemplary embodiment will now be explained with reference to steps 160-194. At step 160, the tubular conduit 70 receives diesel fuel therein. The tubular conduit 70 has a first end 100 and a second end 102. The diesel fuel flows through tubular conduit 70 from first end 100 to second end 102 where it is in fluid communication with temperature sensor 86. At step 162, the controller 90 receives a first signal from the temperature sensor 86 indicative of a temperature of the diesel fuel in the tubular conduit 70, and determines a first temperature value based on the first signal. At step 164, the controller 90 makes a determination as to whether the first temperature value is within a first predetermined temperature range or alternatively, at or below a set point temperature. This assessment of the first temperature is to determine whether the fuel temperature has reached a temperature where it is desirable to begin evaluation of the cloud point temperature. In one exemplary embodiment, the first predetermined temperature range is a temperature range less than or equal to 10° C. Of course, other temperature ranges are contemplated herein. If the value of step 164 equals "yes", the method advances to step 166. Otherwise, the method returns to step 162. At step 166, the controller 90 generates a first oscillatory signal to induce the electrical speaker 80 to emit an oscillatory sound wave from the first end 100 of the tubular conduit 70 toward the second end 102 of the tubular conduit 70. At step 168, the controller 90 receives a second oscillatory signal from the microphone 84 disposed proximate to the second end 102 of the tubular conduit 70 responsive to the first oscillatory sound wave. At step 170, the controller 90 determines a first phase shift value based on the first and second oscillatory signals. The first phase shift value is indicative of a phase difference between the first and second oscillatory signals. At step 172, the controller 90 generates a signal to induce the thermal device 82 to cool the diesel fuel in the tubular conduit 70. At step 180, the controller 90 receives a signal from the temperature sensor 86 indicative of a temperature of the diesel fuel in the tubular conduit 70, and determines a second temperature value based on the signal from the temperature sensor. At step 182, the controller 90 makes a determination as to whether the second temperature value is less than or equal to the first temperature value minus 2° C. or other suitable decrement value. If the value of step 182 equals "yes", the method advances to step 184. Otherwise, the method returns to step 180. At step 184, the controller 90 generates a third oscillatory signal to induce the electrical speaker 80 to emit a second oscillatory sound wave from the first end 100 of the tubular conduit 70 toward the second end 102 of the tubular conduit 70. At step 186, the controller 90 receives a fourth oscillatory signal from the microphone 84 disposed proximate to the second end 102 of the tubular conduit 70 responsive to the second oscillatory sound wave. At step 188, the controller 90 determines a second phase shift value based on the third and fourth oscillatory signals. The second phase shift value is indicative of a phase difference between the oscillatory signals. At step 190, the controller 90 makes a determination as to whether the following condition is present: first phase shift value—second phase shift value is greater than a threshold phase shift value. The threshold phase shift value is selected so as to be indicative that the diesel fuel is at a cloud point temperature. If the value of step 190 equals "yes", the method advances to step 192. Otherwise, the method returns to step 180. At step 192, the controller 90 sets a cloud point temperature value equal to the second temperature value and (i) displays the cloud point temperature value on the display device 92, and (ii) stores the cloud point temperature value in the memory device 94. At step 194, the controller 90 stops generating the signal to induce the thermal device 82 thereby terminating cooling of the diesel fuel in the tubular conduit 70. The steps of the method may be repeated continuously in conjunction with the operation of vehicle 10 or engine 20.

Because the thermal device 82 may be controlled to either heat or cool the conduit, the essence of the embodiment described above is believed to consist of utilizing two phase shift values associated with two fuel temperature to determine a cloud point temperature of the diesel fuel. This may be generalized wherein the controller is configured to determine a first temperature value based on a first temperature signal and a first phase shift value associated therewith, change the temperature of the diesel fuel in the conduit and determine a second temperature value based on a second temperature signal and a second phase shift value associated therewith, and to set the cloud point temperature value equal to one of the first temperature value or the second temperature value based on a threshold phase shift value related to the first temperature value and the second temperature value.

Figure 6:
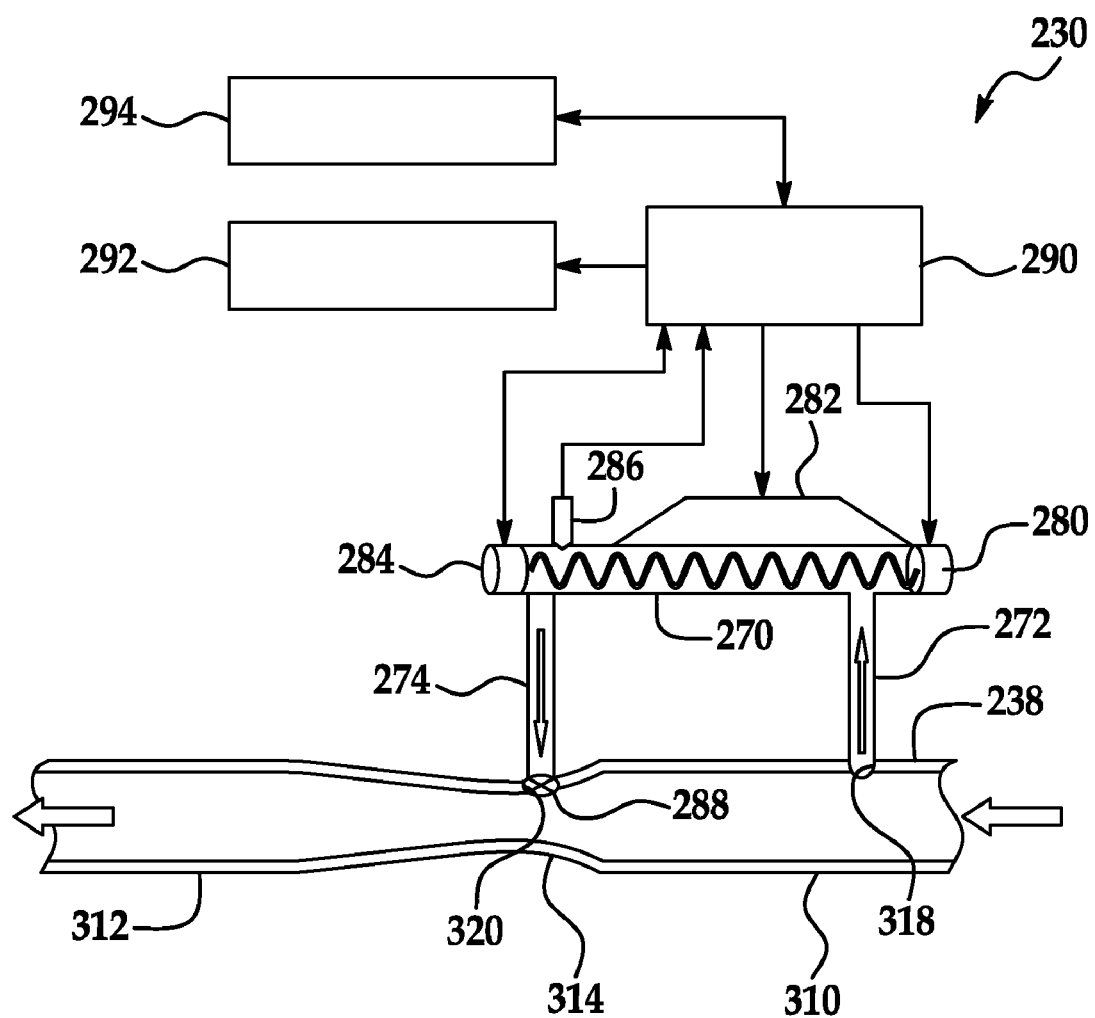
FIG. 6 is a schematic of another cloud point monitoring system, in accordance with another exemplary embodiment.

Referring to FIG. 6, a cloud point monitoring system 230 which determines a cloud point temperature of diesel fuel in accordance with another exemplary embodiment of the invention will now be explained. The elements of system 230 are identical to and have the same function as those of system 30 above, except as noted below, and have been indexed by 200 for clarity.

The cloud point monitoring system 230 includes tubular conduits 270, 272, 274, an electrical speaker 280, a thermal device 282, a microphone 284, a temperature sensor 286, a filter 288, a controller 290, a display device 292, and a memory device 294. The cloud point monitoring system 230 is fluidly coupled to the diesel fuel conduit 238 and receives a portion of the diesel fuel flowing through the diesel fuel conduit 238 to determine the cloud point temperature of the diesel fuel. The diesel fuel conduit 238 includes end portions 310, 312 and a venturi portion 314 disposed between the end portions 310, 312.

The primary difference between the cloud point monitoring system 230 and the cloud point monitoring system 30 is that the tubular member 270 may have a shorter longitudinal length than the tubular member 70. Further, the tubular member 274 extends from the tubular member 270 to the venturi portion 314 of the diesel fuel conduit 238, instead of the tubular member 74 extending from the tubular member 70 to the end portion 112 of diesel fuel conduit 38. The operational functionality of the electrical speaker 280, the thermal device 282, the microphone 284, the temperature sensor 286, the filter 288, the controller 290, the display device 292, and the memory device 294, is substantially similar to the operational functionality of the electrical speaker 80, the thermal device 82, the microphone 84, the temperature sensor 86, the filter 88, the controller 90, the display device 92, and the memory device 94, respectively.

The cloud point monitoring systems for determining a cloud point temperature value for diesel fuel of this invention represents a substantial advantage over other systems and methods. In particular, the cloud point monitoring systems disclosed herein provide a technical effect of utilizing a phase shift value indicative of a phase shift of a sound wave propagating through diesel fuel to determine a cloud point temperature value indicating a cloud point temperature of the diesel fuel.

While the acoustic sources, acoustic sensors, temperature sensors and thermal devices are illustrated in the several exemplary embodiments in the respective positions shown with reference to the respective first ends and second ends of the tubular conduits, it is believed that embodiments (not shown) which modify or vary the relative positions of these elements will also function in accordance with the present invention and are within the scope thereof.

While the invention has been described with reference to exemplary embodiments, it will be understood by those skilled in the art that various changes may be made and equivalent elements may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying this invention, but that the invention will include all embodiments falling within the scope of the appended claims. Moreover, the use of the terms, first, second, etc. are used to distinguish one element from another. Furthermore, the use of the terms a, an, etc. do not denote a limitation of quantity, but rather denote the presence of at least one of the referenced items.

What is claimed is:

1. A cloud point monitoring system, comprising:
a conduit, having a first aperture and a second aperture, the apertures configured to admit diesel fuel from a fuel conduit into and through the conduit;
an acoustic source disposed in the conduit and configured to emit an oscillatory sound wave in response to a first oscillatory signal from a controller;
an acoustic sensor disposed in the conduit and spaced from the acoustic source, the acoustic sensor configured to receive the oscillatory sound wave emitted from the acoustic source and to generate a responsive oscillatory signal to the oscillatory sound wave;
a temperature sensor disposed in the conduit and configured to generate a temperature signal indicative of the temperature of the diesel fuel in the conduit;
the controller configured to generate and send the first oscillatory signal to the acoustic source, to receive the responsive oscillatory signal from the acoustic sensor, to determine a phase shift of the sound wave based on the first oscillatory signal and the responsive oscillatory signal, receive the temperature signal from the temperature sensor and to thereby determine a cloud point temperature value associated with the diesel fuel in the conduit based on the phase shift of the oscillatory wave and the temperature signal.

2. The cloud point monitoring system of claim 1, further comprising a thermal device disposed adjacent the conduit configured to cool the conduit in response to a signal from the controller.

3. The cloud point monitoring system of claim 1, wherein the thermal device comprises a Peltier cell.

4. The cloud point monitoring system of claim 1, wherein the phase shift value is indicative of a phase difference between the first and second oscillatory signals.

5. The cloud point monitoring system of claim 1, wherein the controller is configured to determine the cloud point temperature value by determining a temperature value based on the temperature signal and to set the cloud point temperature value equal to the temperature value when the phase shift value is less than or equal to a predetermined phase shift value.

6. The cloud point monitoring system of claim 1, wherein the controller is configured to determine a first temperature value based on a first temperature signal and a first phase shift value associated therewith, change the temperature of the diesel fuel in the conduit and determine a second temperature value based on a second temperature signal and a second phase shift value associated therewith, and to set the cloud point temperature value equal to one of the first temperature value or the second temperature value based on a threshold phase shift value related to the first temperature value and the second temperature value.

7. The cloud point monitoring system of claim 1, wherein the acoustic source is configured to emit the oscillatory sound wave at a first predetermined frequency.

8. The cloud point monitoring system of claim 1, further comprising a display device, the controller further configured to induce the display device to display the cloud point temperature value thereon.

9. The cloud point monitoring system of claim 1, further comprising second and third conduits, the fuel conduit having first and second end portions and a restricted portion, the restricted portion being disposed between the first and second end portions, the second conduit routing the portion of the diesel fuel supply from the first end portion through the first aperture into the conduit, the third conduit routing the portion of the diesel fuel in the conduit from the second aperture to the second end portion.

10. The cloud point monitoring system of claim 1, further comprising second and third conduits, the fuel conduit having a first end portion and a venturi portion, the second conduit routing the portion of the diesel fuel supply from the first end portion through the first aperture into the conduit, the third conduit routing the portion of diesel fuel supply in the conduit from the second aperture to the venturi portion.

11. A motor vehicle, comprising:
a diesel engine configured to receive diesel fuel from a fuel conduit; and
a cloud point monitoring system receiving a portion of the diesel fuel from the fuel conduit, the cloud point monitoring system comprising:
a conduit, having a first aperture and a second aperture, the apertures configured to admit diesel fuel from the fuel conduit into and through the conduit;
an acoustic source disposed in the conduit and configured to emit an oscillatory sound wave in response to a first oscillatory signal from a controller;
an acoustic sensor disposed in the conduit and spaced from the acoustic source, the acoustic sensor configured to receive the oscillatory sound wave emitted from the acoustic source and to generate a responsive oscillatory signal to the oscillatory sound wave;
a temperature sensor disposed in the conduit and configured to generate a temperature signal indicative of the temperature of the diesel fuel in the conduit;
the controller configured to generate and send the first oscillatory signal to the acoustic source, to receive the responsive oscillatory signal from the acoustic sensor, to determine a phase shift of the sound wave based on the first oscillatory signal and the responsive oscillatory signal, receive the temperature signal from the temperature sensor and to thereby determine a cloud point temperature value associated with the diesel fuel in the conduit based on the phase shift of the oscillatory wave and the temperature signal.

12. The motor vehicle of claim 11, wherein the cloud point monitoring system further comprises a thermal device disposed adjacent the conduit configured to cool the conduit in response to a fourth signal from the controller.

13. The motor vehicle of claim 11, wherein the thermal device comprises a Peltier cell.

14. The motor vehicle of claim 11, wherein the phase shift value is indicative of a phase difference between the first and second oscillatory signals 12.

15. The motor vehicle of claim 11, wherein the controller is configured to determine the cloud point temperature value by determining a temperature value based on the temperature signal and to set the cloud point temperature value equal to the temperature value when the phase shift value is less than or equal to a predetermined phase shift value.

16. The motor vehicle of claim 11, wherein the controller is configured to determine a first temperature value based on a first temperature signal and a first phase shift value associated therewith, change the temperature of the diesel fuel in the conduit and determine a second temperature value based on a second temperature signal and a second phase shift value associated therewith, and to set the cloud point temperature value equal to one of the first temperature value or the second temperature value based on a threshold phase shift value related to the first temperature value and the second temperature value.

17. The motor vehicle of claim 11, wherein the acoustic source is configured to emit the oscillatory sound wave at a first predetermined frequency.

18. The motor vehicle of claim 11, further comprising a display device, the controller further configured to induce the display device to display the cloud point temperature value thereon.

19. The motor vehicle of claim 11, further comprising second and third conduits, the fuel conduit having first and second end portions and a restricted portion, the restricted portion being disposed between the first and second end portions, the second tubular conduit routing the portion of the diesel fuel supply from the first end portion through the first aperture into the conduit, the third conduit routing the portion of the diesel fuel in the conduit from the second aperture to the second end portion.

20. The motor vehicle of claim 11, further comprising second and third conduits, the fuel conduit having a first end portion and a venturi portion, the second conduit routing the portion of the diesel fuel supply from the first end portion through the first aperture into the conduit, the third conduit routing the portion of the diesel fuel supply in the conduit from the second aperture to the venturi portion.

21. A cloud point monitoring system, comprising:
a conduit, having a first aperture and a second aperture, the apertures configured to admit diesel fuel from a fuel conduit into and through the conduit;
an acoustic source disposed in the conduit;
an acoustic sensor disposed in the conduit and spaced from the acoustic source; and
a temperature sensor disposed in the conduit;
the controller configured to generate and send a first oscillatory signal to the acoustic source, to receive a responsive oscillatory signal from the acoustic sensor and receive a temperature signal from the temperature sensor and to thereby determine a cloud point temperature value associated with the diesel fuel in the conduit, wherein the cloud point temperature value is determined based on a phase shift of the first oscillatory signal and the responsive oscillatory signal.

* * * * *